(12) United States Patent
Höver et al.

(10) Patent No.: US 10,349,869 B2
(45) Date of Patent: Jul. 16, 2019

(54) METHOD AND SYSTEM FOR AN ASSESSMENT OF A MOVEMENT OF A LIMB-RELATED POINT IN A PREDETERMINED 3D SPACE

(71) Applicant: Hocoma AG, Volketswil (CH)

(72) Inventors: Raphael Höver, Zurich (CH); Peter Fisch, Hombrechtikon (CH)

(73) Assignee: HOCOMA AG, Volketswil (CH)

( * ) Notice: Subject to any disclaimer, the term of this patent is extended or adjusted under 35 U.S.C. 154(b) by 322 days.

(21) Appl. No.: 15/300,438

(22) PCT Filed: Mar. 31, 2015

(86) PCT No.: PCT/EP2015/057019
§ 371 (c)(1),
(2) Date: Sep. 29, 2016

(87) PCT Pub. No.: WO2015/150381
PCT Pub. Date: Oct. 8, 2015

(65) Prior Publication Data
US 2017/0112417 A1    Apr. 27, 2017

(30) Foreign Application Priority Data
Mar. 31, 2014   (EP) ..................................... 14162652

(51) Int. Cl.
*A61B 5/00* (2006.01)
*A61B 5/11* (2006.01)

(52) U.S. Cl.
CPC .......... *A61B 5/1126* (2013.01); *A61B 5/1122* (2013.01); *A61B 5/1124* (2013.01); *A61B 5/1127* (2013.01); *A61B 5/742* (2013.01)

(58) Field of Classification Search
CPC ... A61B 5/1121; A61B 5/1122; A61B 5/1124; A61B 5/1126; A61B 5/1127; A61B 5/742
See application file for complete search history.

(56) References Cited

U.S. PATENT DOCUMENTS

| 4,605,373 A * | 8/1986 | Rosen | ..................... G09B 23/32 434/274 |
| 7,292,151 B2 * | 11/2007 | Ferguson | ............. A61B 5/1124 340/407.1 |

(Continued)

FOREIGN PATENT DOCUMENTS

| CN | 103315744 A | 9/2013 |
| CN | 103598889 A | 2/2014 |

(Continued)

OTHER PUBLICATIONS

Klopcar, N. et al., "Kinematic Model for Determination of Human Arm Reachable Workspace", Meccanica, 2005, pp. 203-219, vol. 40.

(Continued)

*Primary Examiner* — Max F Hindenburg
(74) *Attorney, Agent, or Firm* — The Webb Law Firm (57) ABSTRACT

A method for an assessment of a movement of a limb-related point in a predetermined 3D space effected by a user displacing the limb in the 3D space is provided. The method includes the steps of providing display surfaces in the 3D space around the user, providing a limb position point connected to a portion of the user's limb associated to the limb-related point, and providing sensors to detect the limb position point in the 3D space in relation to the joint. A computer program calculates a direction defined by a straight line between the joint and the limb-related point and provides a representation of the position of the limb-related point in the 3D space as a function of a distance between the joint and the limb-related point on one of the display surfaces on the line.

16 Claims, 5 Drawing Sheets

(56) References Cited

U.S. PATENT DOCUMENTS 9,597,015 B2 * 3/2017 McNames ............ A61B 5/1071
2013/0171601 A1 7/2013 Yuasa et al.

FOREIGN PATENT DOCUMENTS

EP 2660742 A1 11/2013
WO 2011004403 A1 1/2011

OTHER PUBLICATIONS

Klopcar, N. et al., "A kinematic model of the shoulder complex to evaluate the arm-reachable workspace", J Biomech, 2007, pp. 86-91, vol. 40.

Kurillo, G. et al., "Development and Application of Stereo Camera-Based Upper Extremity Workspace Evaluation in Patients with Neuromuscular Diseases", PLoSOne, Sep. 2012, pp. 1-10, vol. 7, Issue 9, e45341.

Rudhe, C. et al. "Reliability of movement workspace measurements in a passive arm orthosis used in spinal cord injury rehabilitation", Journal of NeuroEngineering and Rehabilitation, 2012, 8 pages, vol. 9.

* cited by examiner

METHOD AND SYSTEM FOR AN ASSESSMENT OF A MOVEMENT OF A LIMB-RELATED POINT IN A PREDETERMINED 3D SPACE

CROSS-REFERENCE TO RELATED APPLICATIONS

This application is the United States national phase of International Application No. PCT/EP2015/057019 filed Mar. 31, 2015, and claims priority to European Patent Application No. 14162652.3 filed Mar. 31, 2014, the disclosures of which are hereby incorporated in their entirety by reference.

TECHNICAL FIELD

The present invention relates to a method and a system for an assessment of a movement of a limb-related point in a predetermined 3D space.

BACKGROUND OF THE INVENTION

Gregorij Kurillo, Jay J. Han, Richard T. Abresch, Alina Nicorici, Posu Van and Ruzena Bajcsy have published the article "Development and Application of Stereo Camera-Based Upper Extremity Workspace Evaluation in Patients with Neuromuscular Diseases" on PLOSONE (Volume 7, Issue 9, e45341, www.plosone.org) (17 Sep. 2012), disclosing a stereo camera-based reachable workspace analysis system which is capable of distinguishing individuals with varying degrees of proximal upper limb functional impairments. Prescribed movements are performed along a workspace envelope. The user is guided by a therapist on what movements to do. The results are used to derive sphere segments as a model-based assumption. The disclosed stereo camera-based reachable workspace acquisition system combined with customized 3D workspace analysis algorithm was compared against a sub-millimeter motion capture system. The stereo camera-based system was robust, with minimal loss of data points, and with the average hand trajectory error of about 40 mm, which resulted to about 5% error of the total arm distance. For a number of persons, the workspace envelope surface areas generated from the 3D hand trajectory captured by the stereo camera were compared. Normalization of acquired reachable workspace surface areas to the surface area of the unit hemi-sphere allowed comparison between subjects. The healthy group's relative surface areas were about 0.618 and 0.552, for the right and left arm, respectively, while the surface areas for the individuals with neuromuscular diseases ranged from 0.03 and 0.09 (the most severely affected individual) to 0.62 and 0.50 (very mildly affected individual), for the right and left arm, respectively. Neuromuscular patients with severe arm weakness demonstrated movement largely limited to the ipsilateral lower quadrant of their reachable workspace.

The findings indicate that the proposed stereo camera-based reachable workspace analysis system is capable of distinguishing individuals with varying degrees of proximal upper limb functional impairments. The method to intuitively display and effectively analyze reachable workspace complements traditional upper limb functional assessments and allows quantifying and monitoring upper limb functions.

Claudia Rudhe, Urs Albisser, Michelle L Starkey, Armin Curt and Marc Bolliger have published the article "Reliability of movement workspace measurements in a passive arm orthosis used in spinal cord injury rehabilitation" in Journal of NeuroEngineering and Rehabilitation 2012, 9; 37 (http://www.jneuroengrehab.com/) (9 Jun. 2012). The arm of the user is moved to specific points in the reachable workspace to calibrate a model that approximates the workspace geometry (box, ellipsoid, etc.). As robotic and non-robotic training devices are increasingly being used in the rehabilitation of upper limb function in subjects with neurological disorders, the article provides an evaluation of the reliability of movement measures as assessed with an ArmeoSpring system (provided by Hocoma AG, Switzerland) for the application to the rehabilitation of patients suffering from cervical spinal cord injury (SCI).

Reliability (intra- and inter-rater reliability) of the movement workspace (representing multiple ranges of movement) and the influence of varying seating conditions (5 different chair conditions) was assessed in twenty control subjects. In eight patients with cervical SCI the test-retest reliability (tested twice on the same day by the same rater) was assessed as well as a correlation of the movement workspace to retrieve self-care items as scored by the spinal cord independence measure (SCIM 3). Although the used movement workspace in the tested device has the shape of a cube instead of the anatomical spherical shape the findings were found to be related to clinical outcomes. The workspace volume was calculated from the data provided by the Armeo device and be followed over time to document changes during the course of rehabilitation.

The movement workspace is a multiple joint measure and does not assess the maximal shoulder movement capacity in a single direction as assessed in a single joint range-of-motion measurement. However, the reliability information from this more functional movement seems to be very good compared to, for example, single joint goniometry measurements of the shoulder. Reliability studies for goniometry measurements in the shoulder have a large intra- and inter-rater variability in results.

Klopcar N, Tomsic M and Lenarcic J have published the article "A kinematic model of the shoulder complex to evaluate the arm-reachable workspace." in J Biomech 2005, 40:86-91, disclosing computing a reachable workspace of the arm movement of a user. Klopcar N and Lenarcic J have also published the article "Kinematic Model for Determination of Human Arm Reachable Workspace" in Meccanica (2005) 40:203-219. Said article discloses, especially in its FIGS. 10 and 11 and the relating description, the computed reachable workspace of the arm movement of a user.

A general training apparatus and corresponding method performed using such a training apparatus can be found in EP 2 660 742 from the applicant, inter alia used as means of support to provide for physiotherapy of the back of a person Further similar devices are disclosed in US 2013/171601 and WO2011/004403.

SUMMARY OF THE INVENTION

The prior art provides a method of assessment of the mobility, especially the workspace, of a limb, especially an arm, of a person. Based on the prior art, it is an object of the present invention to improve the method, inter alia accuracy, providing a better assessment of the mobility. It is a further object to improve the data acquisition by providing an intuitive workflow and visualization of the area already swept by the limb.

The method for an assessment of a movement of a limb-related point in a predetermined 3D space effected by a user displacing said limb in the 3D space comprises several steps. The displacement can happen around a joint or freely in the 3D space. The chosen limb of the user is provided with a limb position point connected to a predetermined portion of the limb which is associated to the limb-related point. The user is positioned in a measurement environment, comprising a computer having a processor, memory and a computer program to execute several steps of the method, a sensor arrangement adapted to detect movement of the limb position point within the predetermined 3D space and being connected to the computer and one or more display surfaces being connected to the computer. The user is positioned in front of one or more display surfaces around the 3D space, possibly between the display surfaces. The user position can be explicitly defined or it can only be the end effector which is taken into account. The chosen limb of the user, e.g. the entire arm, is provided with a limb position point connected to a predetermined portion of the limb which is associated to the limb-related point. When the chosen limb is the entire arm, the limb-related point may be the hand which is to be moved in the 3D space; and the limb position point may be an element allowing to identify the position of this point in relation to the hand which can be the limb position point. The computer is connected with sensors adapted to detect the position of the limb position point in the 3D space itself or in relation to the joint, the user is prompted to move the limb while, based on the acquired data from the sensor arrangement and the relation of the positions of the limb position point and the limb-related point, the computer program is adapted to calculate and store the position of the limb-related point in the 3D space and a 2+1D representation of the 3D space and to provide a representation of the position of the limb-related point on one of the display surfaces based on the 2+1D representation. This step of the method may be repeated using different 2+1D representations and different (2D) display surfaces in order to obtain a better accuracy of the assessment of the mobility in the 3D space. In a further step the computer may be adapted to calculate a consistent representation of the 3D workspace from the data stored in the previous steps. In a further step the computer may be adapted to calculate a representation of a 3D workspace that is a subset of the measured workspace in terms of removing a shell such that the points in this workspace are more easily reachable for the user, or a representation of a 3D workspace that is larger than the measured 3D workspace by adding a shell region such that the points in this workspace are more difficult to reach for the user.

The computer can also store the direction defined by the straight line between the joint, which is in the explanation of this paragraph the shoulder, and the end effector position. This is in the 3D space a function of the distance from said joint and thus from the local z-coordinate or in other words a distance on that line.

In fact, the calculating step, using the computer program adapted thereto, determines a value of a first function of the position of the limb-related point, and the representation of the position of the limb-related point in the 3D space as a second function of said value of the first function of the position of the limb-related point on one of the display surfaces. The description revert to two embodiments, wherein in one embodiment the first function relates to Cartesian 2D coordinates and the second function is a distance from a plane determined by this first function plane. It is noted that the plane is not necessarily flat. In the other embodiment described here the first function relates to a direction starting from a central point as a joint of the user and the second function is the distance of the limb point from the originating point. Of course other functions can be chosen to obtain the same result with the only prerequisite that the first function defines a specific position/orientation of the limb point and the second function allows an assessment of the movement of said limb point by the user.

The intuitive visualization of the assessment of the 3D workspace is supported by providing a real-world task to prompt the user, e.g. painting of a wall in a room with a brush. Therefore a user or patient intuitively knows what to do. The representation on the display surface comprises spots that are placed at a 2D location based on the 2D component of the 2+1D representation of positions of the limb-related point that were obtained during this or previous steps of the method, while one or more visual properties of the spot, e.g. color, hue, brightness, opacity, is based on the 1D component of the 2+1D representation of positions of the limb-related point. In a simple embodiment, the 3D space may be a cube in front of the user, the 2+1D representation may result from parallel projection towards the back side of the cube, i.e.—when assuming a Cartesian coordinate system with the back wall parallel to the x-y plane—a limb-related point within the cube, the x- and y-coordinates constitute the 2D part of the 2+1D representation, while the z-coordinate constitutes the 1D part of the 2+1D representation. Worded differently, when the user positions the limb such that the limb-related point is at a certain (x,y,z) position, a spot is displayed at a location corresponding to (x,y) on the display surface with a color hue corresponding to (z). As the assessment of mobility requires the user to reach as far as possible towards the back wall the spot is repainted when the limb-related point assumes the same (x,y) position at a later time during the assessment with a (z) component closer to the back wall. Because the limb-related point may not assume all positions during one assessment certain locations on the display surface may not be painted with a spot. The spot has a finite size corresponding to a desired accuracy for the method, e.g. between 5 and 50 mm, typically 20 mm for assessment of the hand workspace.

A further advantage of the method according to the invention is due to the fact that the representation of the 3D area already swept by the arm is easily understandable on a 2D display surface, especially on a plurality of 2D computer screen providing a display surfaces representing the 3D space. The representation comprises colored spots on walls. The opacity of color hue indicates the depth, i.e. the reach of the arm-function. This avoids the visualization of complex 3D structures.

The invention is not restricted to cubic 3D spaces and parallel projection onto the cube's sides. For example, the 3D space may be any simply connected region of three dimensional space, the projection may use any plane in three dimensional space with an orthogonal or inclined vector along which the third coordinate is measured. Also non-linear and curved mapping of the 3D space to 3 coordinates is possible, esp. including polar or spherical coordinates.

The method according to the invention can be applied for any limb and for a plurality of position measurements.

If performing multiple measurement steps, each provides a part of the workspace boundaries in the form of a usually curved, finite 2D surface in the 3D space. In an additional step these surface parts can be merged together. In an alternative approach all positions of the limb-related point that were assumed during the measurement step(s) are pooled and the computer is adapted to calculate the hull of this cloud using standard mathematical methods.

The advantage of the method is inter alia that it is a purely data-driven approach without the need of using shape primitives like boxes or spheres of the workspace. Each (x,y) position or direction of the limb of the user is associated to a specific surface portion of one of the 2D screens thus representing the real person's workspace with high accuracy. The use of different thresholds to show the possibilities of movement of a user in a specific direction is similar to start with a constrained bubble or sphere at the minimal distance around the shoulder. Then, when the user is pushing his arm in any specific direction and is going beyond the initial threshold being synonym to a white (or black) background, the color of the screen changes at that spot becoming darker (lighter) or a different color depending on the distance between shoulder and hand achieved. The same function can be achieved, if the position of the spot on the display screen is only related to the x,y position of the end-effector and the z position, i.e. the distance to the display screen or another relevant level or section parallel to the screen, would enable that the spot becomes darker (lighter) or a different color depending on the distance between the hand and a reference level.

Time effort for the assessment is tuned by selecting different "brush diameters" or nozzle spray areas, which can be visibly or invisibly represented by the border of the surface portion. This is equivalent to trade usability and speed against accuracy to optimize clinical use. Said larger brush areas can also be applied within one single assessment to different directions to provide a more exact assessment for the front region and to provide a less exact assessment for the top or bottom areas.

A challenge level can be introduced in any exercise by a single parameter value. Most commonly, exercises provide targets that the user has to move to within a workspace, in this case the workspace provided by the method. Any threshold value can be multiplied by e.g. 110%, 120% etc. thus inflating the initial bubble which has to be reached in order to obtain a reaction as a spot on the screen at the beginning and also in order to define the best (=darkest or lightest) color change when the user reaches the highest threshold level which is equivalent to the greatest distance achieved between shoulder and hand. The workspace can be enlarged by including part of the 3D space of a form of a shell around the measured workspace. Similarly the workspace can be shrunk by excluding a shell of the measured workspace. Enlarging the workspace leads to a higher challenge level because targets outside of the workspace that was reached during the measurement have to be reached during the exercise. In contrast, with a shrunk workspace the challenge level is smaller because less distant targets have to be reached.

Beside using a threshold, blowing up or shrinking the workspace can be done using a signed distance function. This avoids the need of a reference point from which the scaling is performed. Here the scattered surface points in the 3D space obtained through a training surface are used to generate a signed distance function. Therefore, all points reached by the user can be described as SDF(x)=0. When using the same visualization for training, a training effect can be obtained by choosing the threshold for a specific colour or hue as SDF(x)=0.01 meter, i.e. the subject has to move another 1 centimeter beyond the previous workspace to obtain the same colour intensity as in the first run. Further details are explained in the article "Reconstruction and Representation of 3D Objects with Radial Basis Functions" by J. C. Carr et al. retrievable under http://www.cs.jhu.edu/~misha/Fall05/Papers/carr01.pdf.

Besides providing a blank surface and to allow the user to reach every direction, it is possible to associate a defined workspace for the user, which he is supposed to reach. In such a scenario all areas outside such a region are not part of the assessment. Such regions can be defined by physical limits, e.g. if the user is at a specific position in the work space, he can only move his hand (and the end effector to a specific extent to his left and right (x,y position) depending inter alia on arm's length. Therefore defining areas "out of bounds" avoids frustration of the user in view of not reachable regions.

A method to effect a training session based on the data gathering as explained above can be part of a training method according to the invention, where the control unit uses the work space to define valid testing points inside the 3D working space and to exclude points which cannot be reached either by device limitations or user movement limitations.

Further embodiments of the invention are laid down in the dependent claims.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF PREFERRED EMBODIMENTS

Figure 1:
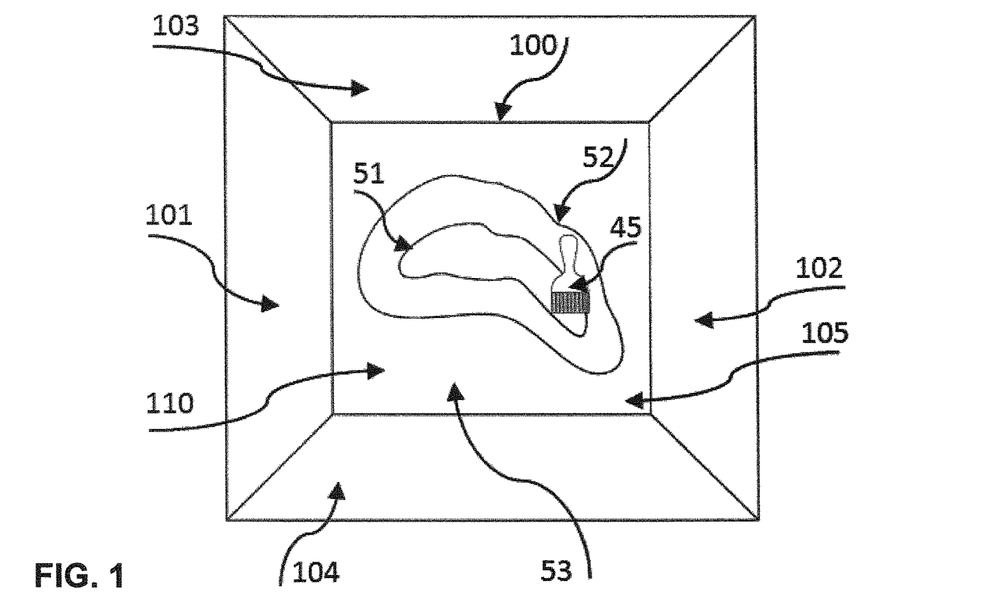
FIG. 1 shows some walls of a display of surfaces of a 3D space, a brush and a painted spot on the front display.
Figure 2:
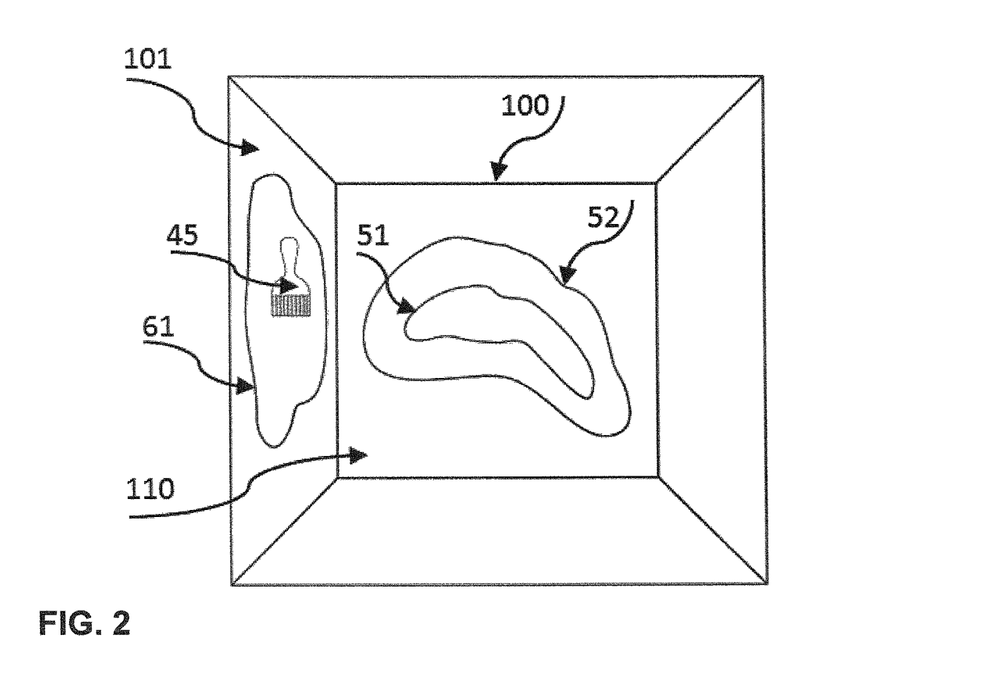
FIG. 2 shows the walls of FIG. 1 with a further spot on the left display.
Figure 3:
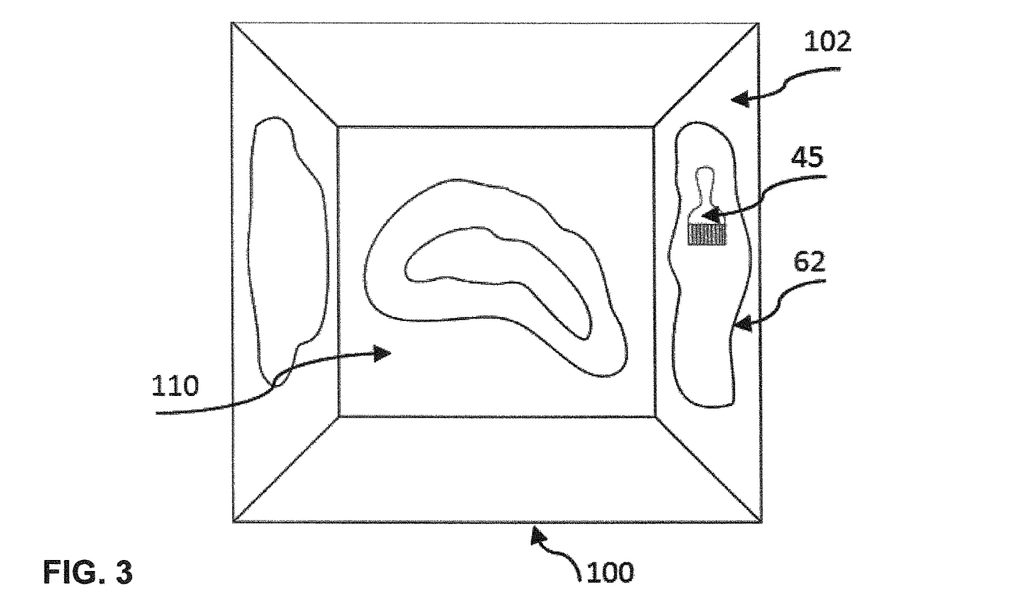
FIG. 3 shows the walls of FIG. 2 with a further spot on the right display.
Figure 4:
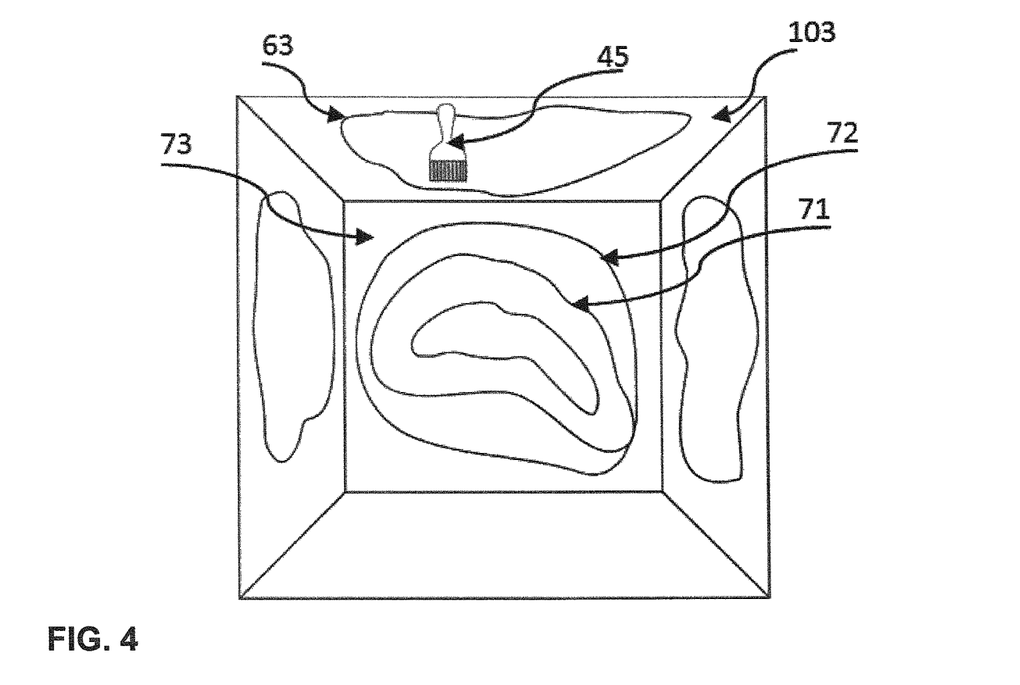
FIG. 4 shows the walls of FIG. 3 with a further spot on the upper display and an explanation of the reachable workspace concept.
Figure 5:
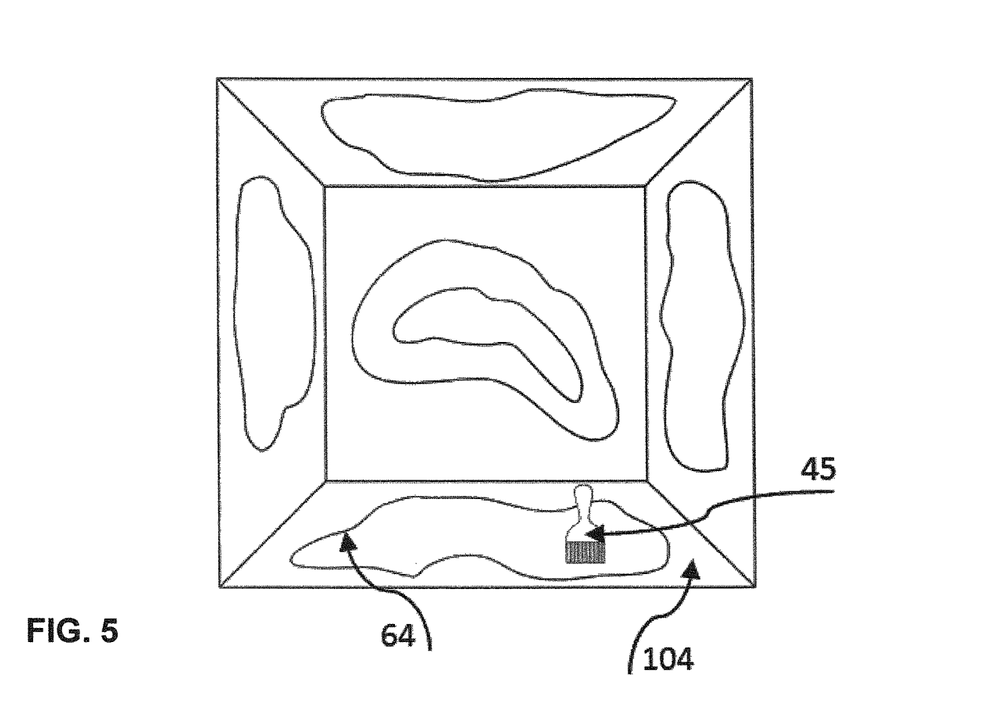
FIG. 5 shows the walls of FIG. 3 with a further spot on the lower display.
Figure 6:
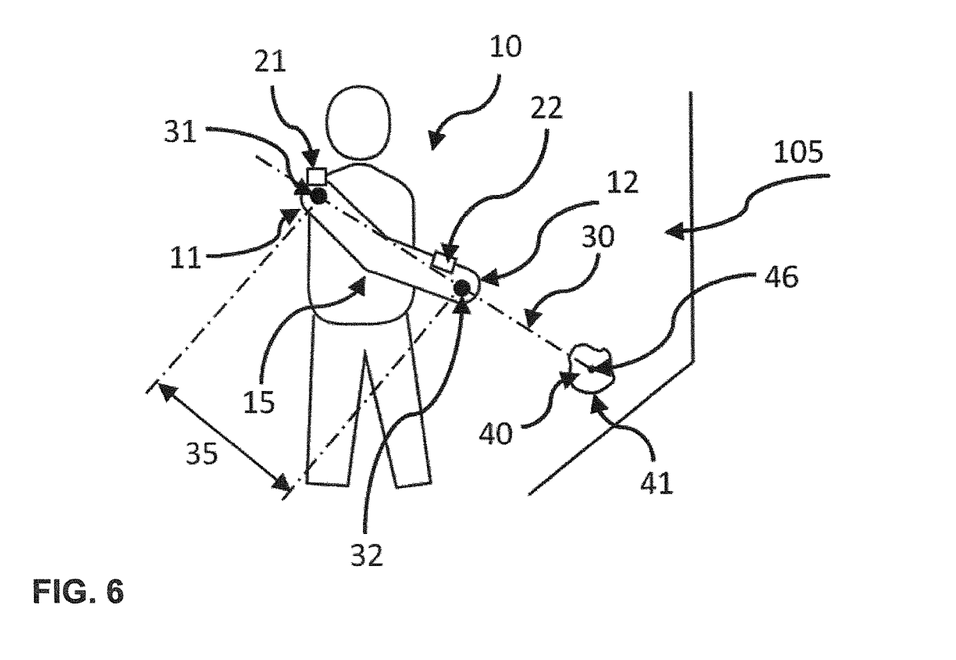
FIG. 6 shows a schematic representation of a user in front of one of the walls.

FIG. 1 shows five walls being displays or screens 100, i.e. hardware providing display surfaces 101, 102, 103, 104 and 105 of a display of surfaces 100 of a 3D space 110, a brush 45 and a painted spot 51 and 52 on the front display 105. FIG. 2 then shows the walls and display surfaces of FIG. 1 with a further spot 61 on the left display 101, FIG. 3 shows the walls and display surfaces of FIG. 2 with a further spot 62 on the right display 102, FIG. 4 shows the walls and display surfaces of FIG. 3 with a further spot 63 on the upper display 103 and FIG. 5 shows the walls and display surfaces of FIG. 4 with a further spot 64 on the lower display 104. The description of FIG. 1 to FIG. 5 will also take into account FIG. 6 showing a schematic representation of a user 10 in front of one of the walls and display surface, here the front display 105.

The embodiment shown here relates to a method for an assessment of a movement of the hand 12 of an arm 15 with the limb-related point 32 in a predetermined 3D space 110 effected by the user displacing said arm 15 as limb in the 3D space 110 around the shoulder 11 (which can also only be the reference frame) as joint 31 allowing said movement. Of course the limb 15 can also be the leg and the foot movement is contemplated. It can also be the head wherein the neck is the joint in question. It is also possible to look at parts of a limb as the underarm wherein the joint is the elbow and the hand movement in relation to the elbow is monitored. In other words, it can also relate to any moveable point with a reference frame fixed to a body part.

User 10 is positioned within a 3D space 110. In the present embodiment the 3D space 110 is surrounded by a display comprising one or more display surfaces 101 to 105 around the 3D space 110 around the user 10, especially positioned around the shoulder 11 as joint 31, Here five display surfaces are shown but it is also possible to close the box by providing a sixth screen behind the user to check its ability to move the arm behind is body, of course without turning the body. It is noted that the shoulder does not need to be inside the workspace. The backplane can be used to assess the back side of the users workspace which can have any location in the 3D space.

The display surfaces can be computer screens or they can be silver screens with associated projectors. It is also possible to provide the display surfaces as virtual representations on glasses to be put in front of the eyes of the user providing the display surface. It is also possible to provide the display surfaces as regions on a computer screen, e.g. in front of the user.

Signal processing is provided by a computer comprising a processor, memory and one or more computer programs. The computer is adapted to send signals to either the screens, the projectors or to the display screen of the glasses for the visualization what will be explained in connection with FIGS. 1 to 5.

Referring to FIG. 6, the user is provided with a hand transmitter 22 as limb position point connected to a predetermined portion of the hand 12 as limb 15 of the user 10 which is associated to the limb-related point 32. The hand transmitter 22 can also be an orthosis and forward kinematic.

The system is equipped with sensors adapted to detect the position of the hand transmitter 22 as limb position point in the 3D space 110; this can be in relation to the shoulder 11 as joint 31 but is not necessarily within such relationship. Since the positional relationship between the hand transmitter 22 and the hand 12 is known, the computer program is adapted to calculate the position of the limb position point 32 (and joint 31, if necessary). In this context hand 12 is represented in the 3D space by the calculated values of limb position point 32.

The position of the shoulder 11 in space can be obtained through different methods. When the Armeo device of Hocoma AG is used (as described in the paper from Claudia Rudhe mentioned in the introduction) then it is possible to calculate the position of the shoulder through its fixation in relation to the device. In an alternative embodiment a shoulder transmitter 21 can be provided so that the user 10 can stand freely in the 3D space 110. The upper body and including the shoulder 11 can also only be used as reference point in a x,y disposition of the method.

The hand transmitter 22 can be one or more lights positioned on the underarm 15 of the user 10 and well known motion capture technology is used to identify the position of the transmitter 22 in space. Within the framework of the present embodiment, knowledge of the position of the underarm is sufficient since it is in a specific distance to the hand as such. Since here, the movement possibilities of the entire arm 15 as limb are studied; the limb position point 32 is "the hand" as such. The hand 12 of the user 10 can hold a handle as provided within the Armeo device of Hocoma AG which is represented as brush 45. Limb position point 22 can be determined to be in the middle of the palm of the hand of the user 10.

It is also possible to use the weight support device (as Armeo by Hocoma AG) and the related sensors in e.g. the joint angle sensors of the device or specific sensors of the device providing the knowledge of the position of said handle of the device in relationship to the limb-related point 32. Based on that it is clear for the person skilled in the art that a number of data acquisition possibilities exist to obtain the necessary 3D data, i.e. the position of the limb position point 32, reflecting the actual position of the hand 12 of the arm 15 in 3D space 110 and the position of the shoulder 11 from the shoulder transmitter 21 in the corresponding embodiments.

The computer program is then adapted either to calculate the direction defined by the straight line 30 between the joint 31 and the limb-related point 32 and to provide a representation of the position of the limb-related point 32 in the 3D space 110 as function of the distance 35 between said joint 31 and the limb-related point 32 on one of the display surface 100-105 on said line 30, or it is adapted either to calculate the position of the hand alone and to provide a representation of the position of the limb-related point 32 in the 3D space 110 as function of the z distance on one of the display surface 100-105.

Initially the result of said calculation is a distance value 35. This distance value 35 can be represented on the related screen surface 105 or it can be maintained as a value without visual representation. Within a different embodiment, the result of the calculation can be the z position of the end effector.

The computer can provide on the related screen surface 105 an associated visible surface portion 40 or it can be maintained invisible or only the surrounding line 41 is represented. At the center of the surface portion 40 is provided a preferably visible point 46. Said point is a cursor which can be a paint brush 45 as shown in FIGS. 1 to 5 or e.g. a spray nozzle or any other visual representation for the user 10 to show him either the direction his arm 15 is pointed or the x,y position of the end effector. In other words the computer program is adapted to visualize the direction of the limb position point 32 seen from the joint 31 on the related surface 105 by the cursor 45 or 46 or visualizes the x,y position of the end effector in front of the related surface 105.

The (screen) surface, onto which the cursor is shown, as indicated in FIGS. 1 to 5, may depend on the x,y,z position of the end-effector or of the direction of the line 30 or a selection of the user or a sequence defined in the workflow. In this direction are to be provided the one or more surfaces 100 to 105 around the 3D space 110 around the user to enable a representation. Preferably at least three planes are provided as the frontal plane 105, a left sagittal plane 101 and a right sagittal plane 102. In a preferred embodiment a top transversal plane 103 and a bottom transversal plane 104 are added and finally it is possible to have a back plane (not shown) so that these six planes are spanning a cube.

The computer program is adapted to determine and store in its memory one or more specific sizes of the surface portion 40. They can be associated to specific directions of the limb position point 32 seen from the joint 31 or they can be associated to specific x,y,z positions of the limb position point 32. In other words, the size of the surface portion 40 can be smaller in front of the user 10, when his arm 15 is directed towards the front screen 105, or the x,y position is such that the position of the effector is just in front of the person, and the size of the surface portion can be bigger, when his arm 15 is directed towards the top screen 103 or when the x,y position is detected such, that the position of the end-effector is high above the training person.

The assessment method of the invention starts from white screen surfaces 53 on screens 101 to 105. Beside white screen surfaces also any neutral color can be used. When the user 10 is then putting forth his hand and reaches out for the virtual wall in front of him the distance 35 between his shoulder 11 and his hand 12 increases and will reach a predetermined threshold distance. If the threshold is chosen 0, then the training person immediately starts painting. Then the computer program triggers the painting function of the brush 45 and colors the surface portion 40. It is then the task of the user to color, if possible the entire surface of the screens 101 to 105. This can only be achieved either if the distance 35 is greater than the said threshold, or if the distance "z" has a specific value. Of course it is also possible to start painting with a threshold/starting value of 0; then the training person immediately starts painting.

It is then clear that the size of the surface portion 40, i.e. the brush size, determines the possible speed of coverage of the screen and the necessary precision of the sweeping movement of the arm 15. A greater surface portion 40 necessitates less precision and allows a faster gathering of data.

The computer program can have stored different threshold distances for different directions. The same is true, if the position z is the basis for the painting action; then the colour resolution can be chosen different for specific x,y values, e.g. in front of the user compared to x,y values related to a positioning of the end effector on the far left or right side of the body of the training person. Directions which are more difficult to achieve can have a lower threshold value than more convenient directions. This can be combined with an array of threshold distances, i.e. that the computer program stores a number of threshold distance for any given direction. This can also be done be providing a first distance value and then determine further threshold values as 110%, 120%, 130% of this initial value and so on. When the user 10 then reaches out for the virtual wall in front of him and "pushes" the virtual brush "against the wall" the distance 35 between his shoulder 11 and his hand 12 increases further and eventually the user 10 will reach further of these predetermined threshold distances. Then preferably the computer program is adapted to change the hue or opacity of the colored spot if the distance 35 between joint 31 and limb position point 32 exceeds one of the further predetermined threshold distances. This is shown in FIG. 1 with two different surface areas. The inner area 51 around the brush 45 is a "darker" area whereas the outer area 52 is the "lighter" area, with the remaining not reached surface 53 remains white. Of course today screens allow for a high number of different color intensities or even different colors as e.g. used for temperature representation, e.g. a blue area 52 for a smaller distance 35 threshold and a red area 51 for a higher distance 35 threshold. In all these cases the function of representation of the distance 35 between the joint 31 and the limb position point 32 is the hue or opacity of the associated surface portion 40 of the surface on said straight line 30.

As explained, it is more intuitive for the user 10, if the function of representation is monotonously increasing or decreasing with said distance 35. The decreasing function can be used with a black screen at the beginning and any outreach of the arm 12 going beyond any one of the thresholds lightens up the screen surface towards grey and finally white, if the last threshold distance is reached.

The explained way of painting on the walls comprises already a further function of the computer program, i.e. any passage of the surface portion 40 over a specific screen portion is memorized, if the distance 35, i.e. the outreach of the arm 15, is greater than one of the memorized thresholds. Then this maximal value for the specific direction is retained. It is possible that the resolution of the position of the cursor 45 is higher than the resolution of the area covered by the surface portion, i.e. when the cursor 45 has a pixel resolution the area covered by the surface portion can have an approximate circle coverage of e.g. eleven pixel or twenty pixel, so that any further sweep of the user can also partly cover a former sweep area.

In order to assess the possibilities of the user 10, the computer is adapted to store in its memory the maximum or minimum value, respectively, of the hue or opacity of any of the associated surface portions 40 for the specific determined size, if the user sweeps more than once over the surface portions 40, either entirely or partly. It is also possible that only the maximum coordinate measured along the plane normal (local normal) is stored.

A challenge level can be introduced in any exercise by a single parameter value. This means that any threshold value is then multiplied by e.g. 110%, 120% etc. thus inflating the initial threshold bubble which has to be reached in order to obtain a reaction as a spot 52 on the screen at the beginning and also in order to define the best (=darkest or lightest) color change, e.g. spot 51, when the user reaches the highest threshold level which is equivalent to the greatest distance achieved between shoulder and hand.

Use of such a single parameter value within a multiplication can set the necessary threshold beyond the maximum reachable distance of the user, defined by his arm length. In such a case, the computer program software is preferably adapted to limit the inflation of workspace so that the inflated workspace always lie inside the device workspace or in other words, all points even in inflated work spaces are physically reachable.

On the other side, the minimum distance 35 to be reached as threshold defines the knowledge of the inner safety region, i.e. the region close to the body of the user 10 which is not to be assessed as assumptions about the location of the patient's body give sufficient information.

Within FIG. 4 is represented the concept of the reachable workspace. Besides providing a blank surface 53 as in FIG. 1 and to allow the user to reach every direction, it is possible to associate a defined delimited workspace 72 for the user 10, which he is supposed to reach starting from an already reached surface 71. Here, only one shading is used in an embodiment where the reaction of the system is "reached" or "not reached" which means that either the minimal threshold distance was reached at a given surface portion 40 or not. In such a scenario all areas 73 outside such a region 72 are not part of the assessment. They should be tainted in a different shade to clearly show the user 10 that he is not supposed to move the brush 45 and thus his arm 15 in this direction. This can be due to reasons within the framework of the exercise or simply, because the training device or the disposition of the user does not allow reaching such areas 73 outside the delimitation 72.

Artifacts due to rapid movements of the user 10 can be suppressed in the resulting workspace using low-pass filters. This is equivalent to the effect that the "paint" in the "brush"

46 is given a viscosity and is only applied (and thus checked) against the position data by the computer after a specific predetermined time, so that the user has to slowly sweep the cursor 45 over the wall to obtain the color or hue change.

Connected with the method is a system for the assessment of a movement of a limb-related point 32 in a predetermined 3D space 110 effected by a user displacing said limb 15 in the 3D space 110 around a joint 11 allowing said movement. Such a system as shown in the schematic representation of FIG. 7 comprises a computer 200 having a processor, memory 201, keyboard or input means 202 and a computer program running on that computer. The system further comprises one or more display surfaces 101 to 105 arranged around the 3D space 110 around the user 10, especially around the shoulder 11 in the present embodiment. A limb position sensor 122 is provided and adapted to receive via wireless or wire-bound transmittal means 222 position data relating to the limb position point 22 connected to a predetermined portion of the arm 15 of the user 10 which is associated to the hand as the limb-related point 32. A further joint sensor 121 is provided to receive position data related to the shoulder via wireless or wire-bound transmittal means 221, depending if a specific shoulder transmitter 21 is used or position data from a weight relief mechanism as Armeo are provided.

Figure 7:
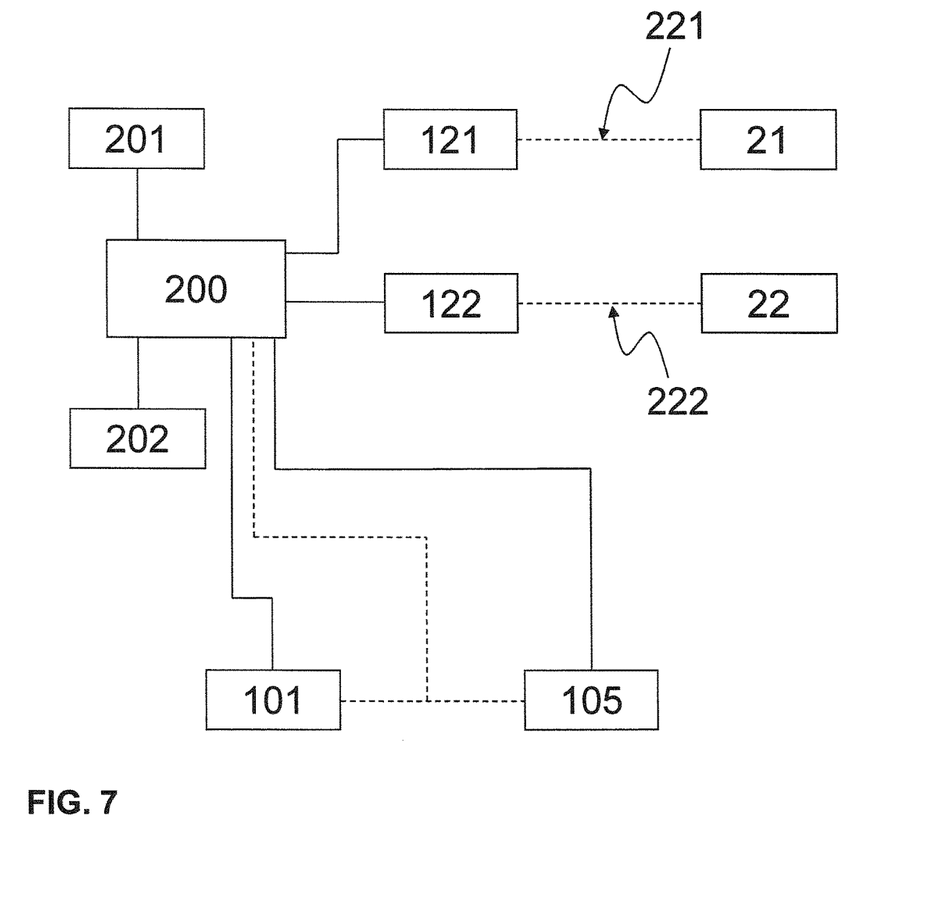
FIG. 7 shows a representation of parts of the system to perform the assessment.

Then the computer program in computer 200 is adapted to calculate the direction defined by the straight line 30 between the shoulder 11 and the limb-related point 32 and control signals are generated and transmitted to the screens to provide a representation 45 of the position of the limb-related point 32 in the 3D space 110 as function of the distance 35 from said shoulder 11 on one of the display surface 101 to 105 on said line 30. The different thresholds as mentioned above can be entered via input means 202 and stored in memory 201. The same is true for different degrees of hue and opacity and the memorized sweeps of the user over the 2D surface of the screens 101 to 105.

Within another embodiment of the system for the assessment of a movement of a limb-related point 32 in a predetermined 3D space 110 effected by a user displacing said limb 15 in the 3D space 110 allowing said movement. Such a system as shown in the schematic representation of FIG. 7. The system further comprises one or more display surfaces 101 to 105 arranged around the 3D space 110 around the user 10. A limb position sensor 122 is provided and adapted to receive via wireless or wire-bound transmittal means 222 position data relating to the limb position point 22 connected to a predetermined portion of the arm 15 of the user 10 which is associated to the hand as the limb-related point 32. Then the sensors take x,y values of the position of the hand via the limb position point 22 to enable "painting" using the z value of the position of the hand in the 3D space.

Then the computer program in computer 200 is adapted to calculate the position of the limb-related point 32 and control signals are generated and transmitted to the screens to provide a representation 45 of the position of the limb-related point 32 in the 3D space 110 as function of the x,y, position and the z distance 35 from a specific section on one of the display surface 101 to 105. The different thresholds as mentioned above can be entered via input means 202 and stored in memory 201. The same is true for different degrees of hue and opacity and the memorized sweeps of the user over the 2D surface of the screens 101 to 105.

The mathematical concept starts with a position of the hand or limb-related point in the 3D space. Then two functions are used to map this 3D-vector value of the hand position into a 2D mapping usually mentioned as (x,y) and a 1D mapping onto (z) wherein the values (x,y) and (z) uniquely define the hand in the 3D space, i.e. the functions define a coordinate system. For each time during the assessment phase, for each spot (x,y), which is a region in the 2D space that is characterized by its position and a brush size, the (z) component is evaluated and stored as (zmax) if it is larger than previous stored (z) at this location. Of course, "larger" does not reduce the generality because the underlying function can be redefined. In order to do that a grid of (x,y) values is predefined, if an (x,y) is never reached during the assessment, its (zmax) is never changed from an initial value, which is different from values that can occur during measurement, e.g. NaN in computer implementations.

The visualisation displays the spot visually at pixel coordinates (a,b) on a display surface with (a,b) as function of (x,y) and colored according to a color index as function of (z). The initial or background color of the display surface is predetermined and chosen and is shown for z=NaN in above example. Therefore, if at a later time (z) at that time is larger than all (z) during this assessment phase, the corresponding spot is repainted with a new value, being a threshold criterion. On the other hand, if at a later time (a,b) are outside of all (a,b) previously encountered, this spot will be colored, being another threshold criterion.

Figure 8:
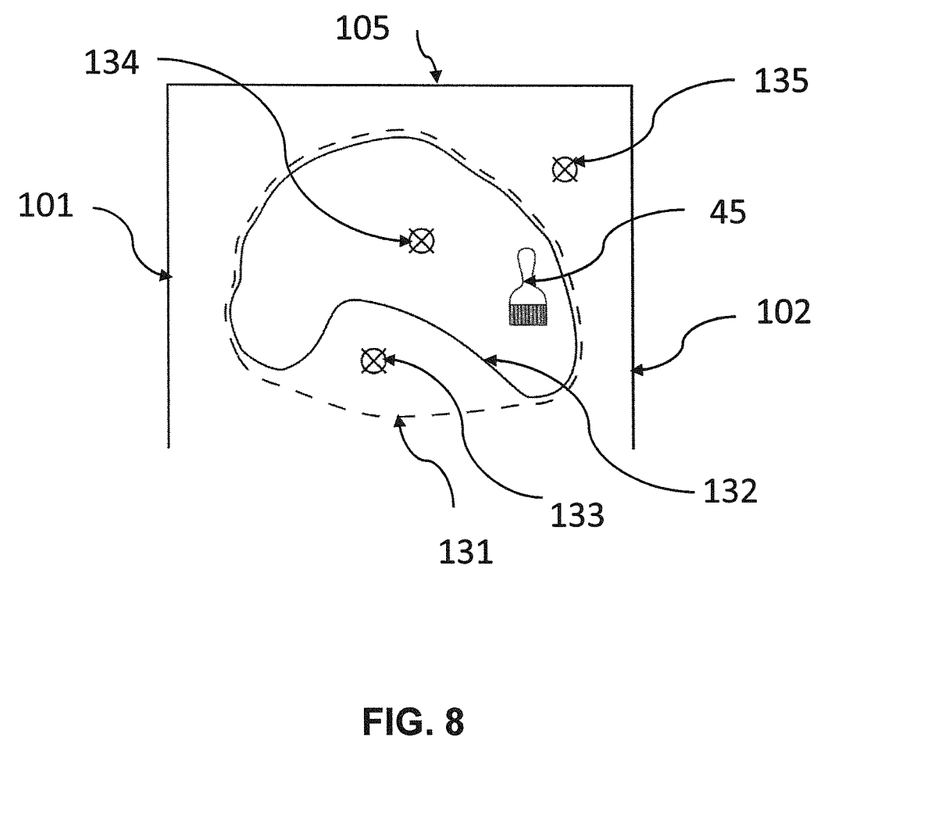
FIG. 8 shows a schematic representation of a view from above onto some walls of FIG. 1 with graphical representation of elements of the reachable workspace as a cross section view.

FIG. 8 shows a schematic representation of a view from above onto some walls 101, 102 and 105 of FIG. 1 with graphical representation of elements of the reachable workspace as a cross section view. Front wall 105 is bordered by the left wall 101 as well as by the right wall 102. The user 10 is positioned below the two side walls 101 and 102 facing the front wall 105. In the initial steps as described with the representations of FIGS. 1 to 5, the user 10 is moving his arm 15 with the virtual brush 45 to "paint" the different walls in front 105, on the right wall 102 as well as on the left wall 101. For the sake of simplicity and understanding, it is not contemplated that the user 10 is painting the bottom wall 104 or the upper wall 103 and FIG. 8 shows a cross section of the view from above e.g. at chest height.

The user 10 generates the representation 72 of the reachable workspace being a closed line 131, shown as dotted line, in the cross section; in other words, the 3D cloud based on 2D paintings as patient workspace has received the reference numeral 131. These values are generated by the user data. On the other side, the device also has its physical limitations, not allowing the user 10 to reach every point in space. These boundaries are not visible when the user strives to paint on opposite walls. But they are quite there, if the user 10 wants to paint in front of his chest; then the mechanical parts of the training device will not allow his hand to reach towards an area and places in front of him.

Therefore, these parts are predetermined exceptions from the workspace and the reachable workspace, the 3D cloud after intersection with the device workspace, is referenced with numeral 132 as closed line. This reachable workspace 132 divides the space (here in the cross section the plane) in two parts. One part is "inside", where reference numeral 134 is related to a target in the reachable part of the workspace, i.e. the user 10 can use the brush 45 to reach this point in space. On the other side there are points 133 "outside" for a target not in the reachable part of the workspace through device limitation and also "outside" points 135 for a target not in the reachable part of the workspace for a specific user.

The method comprising the assessment steps as explained above can be followed by a testing step, comprising generating a first data set of boundaries 132 reachable by a system comprising said sensors 21, 22. Then inside the control unit a second data set of boundaries 131, reachable by the user based on the assessment steps, is created. Then the control unit calculates a third subset of test boundaries as intersection of the first data set with the second data set, to exclude not technically reachable points as points 133 or points 135 outside the subjective range if the user. Thus points 134 are defined which are inside said test boundaries as reachable points and the other points 133, 135 are defined to be outside said test boundaries as not-reachable points.

The training session then comprises providing a target point 134 as part of the subset of reachable points as virtual representation on the one or more display surfaces 101-105 around the 3D space 110 around the user 10 to be reached by the user 10 through movement of a limb position point 22 connected to a predetermined portion of the limb 15 of the user 10 which is associated to the limb-related point 32. If the user 10 is successful to reach the object target point, then he triggers a result event, and optionally the last mentioned two steps are repeated in such a training session with randomly or specifically changing target points 134, especially near the boundaries of reachable points, to push the limits of these boundaries. It is important that the intersection is used to reduce the 3D could of possible targets to the actually reachable target points in the stored 3D space.

| LIST OF REFERENCE SIGNS | |
|---|---|
| 10 | user |
| 11 | shoulder |
| 12 | hand |
| 15 | arm |
| 21 | shoulder transmitter |
| 22 | hand transmitter/limb position point |
| 30 | connection line |
| 31 | joint |
| 32 | limb-related point |
| 40 | surface portion |
| 41 | surrounding line |
| 45 | brush |
| 46 | point |
| 51 | dark area |
| 52 | less dark area |
| 53 | not painted area |
| 61 | spot |
| 62 | spot |
| 63 | spot |
| 64 | spot |
| 65 | spot |
| 71 | reached area |
| 72 | reachable work space |
| 73 | out of bounds area |
| 100 | 3D space walls |
| 101 | left wall |
| 102 | right wall |
| 103 | top wall |
| 104 | bottom wall |
| 105 | front wall |
| 110 | 3D space |
| 121 | joint sensor |
| 122 | limb position sensor |
| 131 | 3D cloud based on 2D paintings (patient workspace) |
| 132 | 3D cloud after intersection with device workspace |
| 133 | target not in the reachable part of the workspace through device limitation |
| 134 | target in the reachable part of the workspace |
| 135 | target not in the reachable part of the workspace for a specific user |
| 200 | computer |
| 201 | memory |
| 202 | input device |

-continued

| LIST OF REFERENCE SIGNS | |
|---|---|
| 221 | joint sensor signal transmittal |
| 222 | limb position sensor signal transmittal |

The invention claimed is:

1. A method for an assessment of a movement of a limb-related point in a predetermined 3D space effected by a user displacing said limb in the 3D space, the method comprising:
   providing a computer comprising a processor, memory and a computer program,
   providing one or more display surfaces around the 3D space around the user,
   providing a limb position point connected to a predetermined portion of the limb of the user which is associated to the limb-related point,
   providing one or more sensors adapted to detect a position of the limb position point in the 3D space in relation to a predetermined plane,
   calculating, using the computer program configured thereto, the position in said plane as a value of a first position function of the position of the limb-related point, and
   providing a representation of the position of the limb-related point in the 3D space which is related to the distance of the limb-related point to that plane as a second position function of said position value of the first position function of the position of the limb-related point on the one or more display surfaces.

2. A method for an assessment of a movement of a limb-related point in a predetermined 3D space effected by a user displacing said limb in the 3D space, the method comprising:
   providing a computer comprising a processor, memory and a computer program,
   providing one or more display surfaces around the 3D space around the user,
   providing a limb position point connected to a predetermined portion of the limb of the user which is associated to the limb-related point, wherein the movement of the limb-related point is effected around a joint allowing said movement,
   providing one or more sensors adapted to detect a position of the limb position point in the 3D space in relation to the joint,
   calculating, using the computer program configured thereto, the direction defined by a straight line between the joint and the limb-related point as a value of a position function of the position of the limb-related point, and
   providing a representation of the position of the limb-related point in the 3D space which is related to the distance of the limb related point to that joint as a distance function of the distance between said joint and the limb-related point on the one or more display surfaces on said straight line defining the direction based on the value of the position function.

3. The method according to claim 1, wherein the one or more display surfaces around the 3D space around the user comprise three to six planes from the group comprising a frontal plane, a left sagittal plane, a right sagittal plane, a top transversal plane, a bottom transversal plane and a back plane.

4. The method according to claim 3, wherein the six planes are spanning a cube.

5. The method according to claim 1, wherein the computer program is adapted to visualize the value of the first position function of the limb-related point on the related display surface by a drawing element from the group comprising a paint brush or spray nozzle, on an associated visible or invisible surface portion.

6. The method according to claim 5, wherein the computer program is adapted to determine and store one or more specific sizes of the surface portion associated to a specific value of the first position function of the limb-related point.

7. The method according to claim 1, wherein the second position function of representation of the limb-related point is the hue or opacity of the associated surface portion of the one or more display surfaces.

8. The method according to claim 6, wherein the second position function of representation is monotonously increasing or decreasing with said value of the second position function.

9. The method according to claim 7, wherein the computer program is adapted to change the hue or opacity if the value of the second position function for the limb position point exceeds one of one or more predetermined thresholds.

10. The method according to claim 9, wherein the one or more predetermined thresholds are predefined and stored in the memory of the computer for a plurality of specific directions.

11. The method according to claim 9, wherein the computer is adapted to store in its memory the maximum and/or the minimum value, respectively, of the hue or opacity of any of the associated surface portions for the specific determined size, if the user sweeps more than once over the surface portions.

12. A system for an assessment of a movement of a limb-related point in a predetermined 3D space effected by a user displacing said limb in the 3D space, comprising
    a computer having a processor, memory and a computer program, one or more display surfaces arranged around the 3D space around the user, a limb position sensor adapted to receive position data relating to a limb position point connected to a predetermined portion of the limb of the user which is associated to the limb-related point in relation to a predetermined plane,
    wherein the computer program is adapted to calculate the position in said plane as a value of a first position function of the position of the limb-related point and to provide a representation of the position of the limb-related point in the 3D space which is related to the distance of the limb-related point to that plane as a second position function of said position value of the first position function of the position of the limb-related point on the one or more display surfaces.

13. The system according to claim 12, further comprising a joint sensor adapted to receive position data related to the joint, wherein the computer program is adapted to calculate the direction defined by the straight line between the joint and the limb-related point as a value of the first position function and wherein the representation of the position of the limb-related point in the 3D space is a function of the distance from said joint on the one or more display surfaces on said straight line.

14. The system according to claim 12, wherein the computer program is adapted to calculate the position in a plane determined by the one or more sensors as the first position function and wherein the representation of the position of the limb-related point in the 3D space is related to the distance to that plane as the second position function of said value of the first position function of the position of the limb-related point on one of the display surfaces.

15. A method for an assessment of a movement of a limb-related point in a predetermined 3D space effected by a user displacing said limb in the 3D space, comprising a number of assessments followed by a number of tests, wherein the assessments comprise:
    providing a computer comprising a processor, memory and a computer program,
    providing one or more display surfaces around the 3D space around the user,
    providing a limb position point connected to a predetermined portion of the limb of the user which is associated to the limb-related point,
    providing one or more sensors adapted to detect a position of the limb position point in the 3D space in relation to a predetermined plane,
    calculating, using the computer program configured thereto, the position in said plane as a value of a first position function of the position of the limb-related point, and
    providing a representation of the position of the limb-related point in the 3D space as a second position function of said position value of the first position function of the position of the limb-related point on the one or more display surfaces,
    wherein the tests comprise:
    generating a first data set of boundaries reachable by a system comprising the sensors,
    generating a second data set of boundaries reachable by the user based on the assessment steps,
    calculating a third subset of test boundaries as an intersection of the first data set with the second data set,
    defining points inside said test boundaries as reachable points and defining points outside said test boundaries as not-reachable points,
    providing a target point as part of the subset of reachable points as virtual representation on the one or more display surfaces around the 3D space around the user to be reached by the user through movement of a limb position point connected to a predetermined portion of the limb of the user which is associated to the limb-related point, and
    triggering a result event, when the user reaches said target point by movement of the limb.

16. The method according to claim 15,
    wherein the last two tests are repeated in a training session with randomly or specifically changing target points or near the boundaries of reachable points.

* * * * *